United States Patent
Thorwart et al.

(10) Patent No.: US 6,815,440 B2
(45) Date of Patent: Nov. 9, 2004

(54) CYCLIC AND HETEROCYCLIC N-SUBSTITUTED α-IMINOHYDROXAMIC AND -CARBOXYLIC ACIDS

(75) Inventors: Werner Thorwart, Hochheim (DE); Wilfried Schwab, Wiesbaden (DE); Manfred Schudok, Hattersheim (DE); Burkhard Haase, Maintal (DE); Eckart Bartnik, Wiesbaden-Delkenheim (DE); Klaus-Ulrich Weithmann, Hofheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 44 days.

(21) Appl. No.: 10/376,287

(22) Filed: Mar. 3, 2003

(65) Prior Publication Data

US 2003/0176432 A1 Sep. 18, 2003

Related U.S. Application Data

(62) Division of application No. 09/780,514, filed on Feb. 12, 2001, now Pat. No. 6,573,277, which is a division of application No. 09/068,497, filed as application No. PCT/EP96/04776 on Nov. 4, 1996, now Pat. No. 6,207,672.

(30) Foreign Application Priority Data

Nov. 13, 1995 (DE) .......................................... 195 42 189
Mar. 28, 1996 (DE) .......................................... 196 12 298

(51) Int. Cl.[7] ...................... C07D 401/02; A61K 31/44; A61K 31/47

(52) U.S. Cl. ............... 514/213.01; 514/217; 514/232.8; 514/291; 514/292; 514/300; 514/301; 514/309; 514/321; 514/322; 514/338; 514/396; 514/411; 514/415; 514/418; 540/577; 540/578; 540/593; 544/111; 546/80; 546/81; 546/113; 546/114; 546/141; 546/207; 546/268.1; 548/303.1; 548/429; 548/431; 548/453; 548/465

(58) Field of Search ............................ 514/231.01, 217, 514/232.8, 291, 292, 300, 301, 309, 321, 322, 338, 396, 411, 415, 418; 540/577, 578, 593; 544/111; 546/80, 81, 113, 114, 141, 207, 268.1; 548/303.1, 429, 431, 453, 465

(56) References Cited

FOREIGN PATENT DOCUMENTS

| JP | A-4-210675 | 7/1992 |
| WO | WO 95/35276 | 12/1995 |
| WO | WO 96/00214 | 1/1996 |

OTHER PUBLICATIONS

M. Vert, "Polymeres Optiquement Actifs–X. Mise en evidence d'une reaction secondaire au cours de la polycondensation en milieu acide du formaldehyde et de la N–tosyl L–Tryosine. Influence sur l'activite optique," *European Polymer Journal*, 8(4), 513–24 (1972) (with Abstract).

C.B. Hudson et al. "The Synthesis and Chemistry of DL–Indoline–2–Carboxylic Acid," *Aust. J. Chem.*, 20, 1935–41 (1967).

B.A. Steinbaugh et al. "Tetrahydroisoquinoline as a Phenylalanine Replacement in Renin Inhibitors," *Bioorganic & Medicinal Chemistry Letters*, 4(16), 2029–33 (1994).

W.C. Patt et al., "Structure–Activity Relationships of a Series of 2–Amino–4–thiazole–Containing Renin Inhibitors," *J. Med. Chem.*, 35, 2562–72 (1992).

H. Kato et al., "Studies on 1–Azabicyclo Compounds. XX. Synthesis of Hexahydroisoquino-[3,2-c][1,4]benzodiazepine and Related Compounds and Formation of 6–Methyl–hexahydro–5H–dibenzo[b,g][1,5]diazacycloundecine from Hexahydroisoquino [3,2-c][1,4]–benzodiazepin–13–one," *Yakugaku Zasshi*, 94, 934–44 (1974).

*Primary Examiner*—Zinna Northington Davis
(74) *Attorney, Agent, or Firm*—Raymond S. Packer

(57) ABSTRACT

Cyclic and heterocyclic N-substituted α-iminohydroxamic and -carboxylic acids

Compounds of the formula I

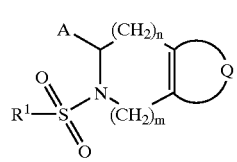

(I)

are suitable for preparing pharmaceuticals for the treatment of disorders in the course of which is involved an increased activity of matrix-degrading metalloproteinases.

19 Claims, No Drawings

CYCLIC AND HETEROCYCLIC N-SUBSTITUTED α-IMINOHYDROXAMIC AND -CARBOXYLIC ACIDS

This is a division of application Ser. No. 09/780,514, filed Feb. 12, 2001, now U.S. Pat. No. 6,573,277, which is a division of application Ser. No. 09/068,497, filed Mar. 9, 1999, which issued as U.S. Pat. No. 6,207,672 on May 27, 2001, and which was a national stage application under 35 U.S.C. 371 of PCT/EP 96/04776, filed Nov. 4, 1996, and claims benefit of priority of German Patent Applications No. 195 42 189.2, filed Nov. 13, 1995, and No. 196 12 298.8, filed Mar. 28, 1996, all of which are incorporated herein by reference.

DESCRIPTION

Cyclic and heterocyclic N-substituted α-iminohydroxamic and -carboxylic acids

The invention relates to cyclic and heterocyclic N-substituted α-iminohydroxamic and -carboxylic acids, to processes for their preparation and to their use as pharmaceuticals.

EP 0 606 046 discloses some arylsulfonamidohydroxamic acid derivatives and their action as matrix metalloproteinase inhibitors.

In the effort to find further efficacious compounds for the treatment of connective tissue disorders, it has now been found that the iminohydroxamic acid derivatives according to the invention are inhibitors of metalloproteinases.

The invention relates to a compound of the formula I

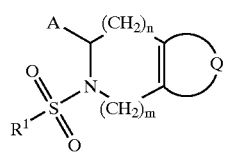

(I)

and/or an optionally stereoisomeric form of the compound of the formula I and/or a physiologically tolerable salt of the compound of the formula I, where in the case i)

$R^1$ is a) a radical of the formula II

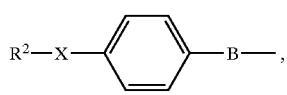

(II)

b) a radical of the formula III

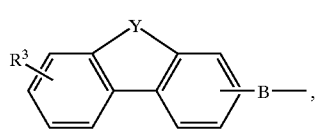

(III)

c) a radical of the formula IV

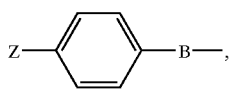

(IV)

where Z is a radical of a heterocycle or a substituted heterocycle such as
      1) pyrrole,
      2) thiazole,
      3) pyrazole,
      4) pyridine,
      5) imidazole,
      6) pyrrolidine,
      7) piperidine,
      8) thiophene,
      9) oxazole,
      10) isoxazole,
      11) morpholine or
      12) piperazine,
  d) naphthyl,
  e) naphthyl, mono- or trisubstituted by $R^2$, or
  f) a radical of the formula V

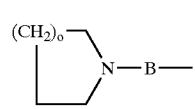

(V)

where o is the number 1 or 2 and one of the carbon atoms in the ring may be replaced by —O— or —S—, and Q as part of the structural formula I

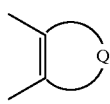

(I)

1) is the structural moiety VI

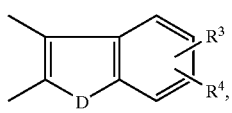

(VI)

2) the structural moiety VII

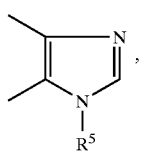

(VII)

3) is the structural moiety VIII

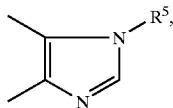
(VIII)

4) the structural moiety IX

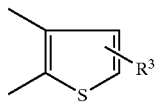
(IX)

or 5) is the structural moiety X

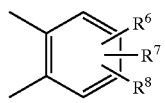
(X)

where D is $NR^4$ or S,
$R^2$ is
  1) phenyl or
  2) phenyl which is mono- to trisubstituted by
    2.1 hydroxyl,
    2.2 —O—$R^{10}$, where $R^{10}$
      1) is $(C_1-C_6)$-alkyl,
      2) is $(C_3-C_6)$-cycloalkyl,
      3) is benzyl or
      4) is phenyl,
    2.3 —COOH,
    2.4 $(C_1-C_6)$-alkyl,
    2.5 $(C_3-C_6)$-cycloalkyl-O-$(C_1-C_4)$-alkyl,
    2.6 halogen,
    2.7 —CN,
    2.8 —$NO_2$,
    2.9 —$CF_3$,
    2.10 —O—C(O)—$R^{10}$ and $R^{10}$ is as defined above,
    2.11 —O—C(O)-phenyl, mono- or disubstituted by $R^3$,
    2.12 —C(O)—O—$R^{10}$ and $R^{10}$ is as defined above,
    2.13 methylenedioxo,
    2.14 —C(O)—$NR^{11}R^{12}$, where
      $R^{11}$ and $R^{12}$ may be identical or different and each is
      1) a hydrogen atom,
      2) $(C_1-C_4)$-alkyl or
      3) benzyl or
      4) $R^{11}$ and $R^{12}$ together with the linking nitrogen atom form a pyrrolidine, piperdine, morpholine or piperazine radical, or
    2.15 —$NR^{13}R^{14}$, where $R^{13}$ is a hydrogen atom or $(C_1-C_4)$-alkyl and
      $R^{14}$ 1) is a hydrogen atom,
        2) is $(C_1-C_4)$-alkyl,
        3) is benzyl,
        4) is —C(O)—$R^{10}$ or
        5) is —C(O)—O—$R^{10}$, $R^3$ and $R^4$ are identical or different and each is
  1) a hydrogen atom,
  2) $(C_1-C_5)$-alkyl,
  3) $(C_1-C_5)$-alkoxy,
  4) halogen,
  5) hydroxyl,
  6) —O—C(O)—$R^{10}$ and $R^{10}$ is as defined above, or
  7) $R^3$ and $R^4$ together form the radical —O—$CH_2$—O—, $R^5$ is
  a) a hydrogen atom,
  b) $(C_1-C_5)$-alkyl or
  c) benzyl, and $R^6$, $R^7$ and $R^8$ are identical or different and each is
  a) a hydrogen atom, or
  b) has, in the case of i), the meaning of $R^2$ under items 2.1 to 2.14, and n is zero, 1 or 2,
m is zero, 1 or 2, the sum of n and m being 1, 2 or 3, or
where in the case ii)
$R^1$ is
  1) phenyl or
  2) phenyl, mono- to trisubstituted by $R^2$, where $R^2$ is as defined for the case i) under items 2.1 to 2.15, Q is the structural moiety X and
$R^6$, $R^7$ and $R^8$ are identical or different and each is defined as above,
n is 1 and
m is 1, or
where in the case iii)
$R^1$, Q, $R^6$, $R^7$ and $R^8$ are identical or different and each has the meaning mentioned for the case ii),
m and n are zero, 1 or 2 and where the meanings of n and m are not identical, and
X is
  a) a covalent bond,
  b) —O—,
  c) —S—,
  d) —S(O)—,
  e) —$S(O)_2$—,
  f) —C(O)— or
  g) —C(OH)—, and
Y is
  a) —O— or
  b) —S—, and
A is HO—NH—C(O)— or HO—C(O)— and
B is a) —$(CH_2)_q$—, where q is zero, 1, 2, 3 or 4, or
  b) is —CH=CH—.

Preference is given to a compound of the formula I and/or a physiologically tolerable salt of the compound of the formula I and/or an optionally stereoisomeric form of the compound of the formula I, where
  $R^1$ in the case i) is a radical of the formula II or III and Q is the structural moiety VI, VII, VIII or X,
  $R^1$ in the case ii) is phenyl or phenyl, mono- to trisubstituted by methoxy, and Q is the structural moiety X, or
  $R^1$ in the case iii) is phenyl, Q is the structural moiety X, n is zero and m is 2, and
  A is HO—NH—C(O)— or HO—C(O)—,
  B is a covalent bond,
  X is an oxygen atom or a covalent bond, and
  $R^2$ is phenyl or phenyl substituted by
    a) hydroxyl,
    b) —O—$R^{10}$, where $R^{10}$ is $(C_1-C_3)$-alkyl or benzyl,
    c) $(C_1-C_2)$-alkyl,
    d) fluorine or chlorine, e) —CN, f) —CF$_3$ or g) NR$^{13}$R$^{14}$, where R$^{13}$ and R$^{14}$ are each (C$_1$–C$_3$)-alkyl, R$^3$, R$^4$, R$^5$, R$^6$, R$^7$ and R$^8$ are identical or different and each is a) a hydrogen atom, b) methoxy, c) methylenedioxo, d) amino or e) hydroxyl.

Particular preference is given to the compounds

R-2-(biphenylsulfonyl)-1,2,3,4-tetrahydroisoquinoline-3-hydroxamic acid,

R-2-(4-chlorobiphenylsulfonyl)-1,2,3,4-tetrahydro-isoquinoline-3-hydroxamic acid, R-2-(4-chlorabiphenylsulfonyl)-1,2,3,4-tetrahydro-isoquinoline-3-carboxylic acid, R-2-(4-phenoxybenzenesulfonyl)-1,2,3,4-tetrahydro-isoquinoline-3-hydroxamic acid, R-2-(4-phenoxybenzenesulfonyl)-1,2,3,4-tetrahydro-isoquinoline-3-carboxylic acid, R-2-(4-(4-dimethylaminophenoxy)benzenesulfonyl)-1,2,3,4-tetrahydroisoquinoline-3-hydroxamic acid, R-2-(4-dimethylaminobiphenylsulfonyl)-1,2,3,4-tetrahydroisoquinoline-3-carboxylic acid, R-2-(4-benzoylphenylsulfonyl)-1,2,3,4-tetrahydro-isoquinoline-3-hydroxamic acid, R-2-(4-methoxybenzenesulfonyl)-7-hydroxy-1,2,3,4-tetrahydroisoquinoline-3-hydroxamic acid, R-2-(4-methoxybenzenesulfonyl)-7-nitro-1,2,3,4-tetrahydroisoquinoline-3-hydroxamic acid, 2-(4-methoxybenzenesulfonyl)-6,7-propylene-1,2,3,4-tetrahydroisoquinoline-1-hydroxamic acid, R-5-(4-methoxybenzenesulfonyl)-4,5,6,7-tetrahydro-1H-imidazo-(4,5-c)-pyridine-6-hydroxamic acid, R-2-(4-methoxybenzenesulfonyl)-1,2,3,4-tetrahydro-9H-pyrido-(3,4-c)-indole-3-hydroxamic acid, R-2-(4-phenoxybenzenesulfonyl)-1,2,3,4-tetrahydro-9H-pyrido-(3,4-c)-indole-3-hydroxamic acid.

Furthermore, particular emphasis is given to those compounds of the formula I where the central carbon atom between amino and acid group is present as R enantiomer.

The term halogen is understood as meaning fluorine, chlorine, bromine or iodine. The term alkyl or alkoxy is understood as meaning radicals whose carbon chain may be straight-chain, branched or cyclic. Cyclic alkyl radicals are, for example, 3- to 6-membered monocycles such as cyclopropyl, cyclobutyl, cyclopentyl or cyclohexyl.

The "heterocycles of the formula V" include, for example, thiomorpholine, piperidine, morpholine or piperazine.

Suitable physiologically tolerable salts of the compound of the formula I are, for example, alkali metal, alkaline earth metal and ammonium salts including those of organic ammonium bases or basic amino acids.

The invention also provides a process for preparing the compound of the formula I and/or a physiologically tolerable salt of the compound of the formula I and/or an optionally stereoisomeric form of the compound of the formula I which comprises a) reacting an imino acid of the formula XI

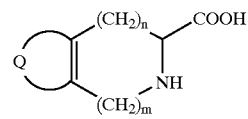

(XI)

where the radical Q and n and m are as defined in the formula I with a (C$_1$–C$_4$)-alcohol or a benzyl alcohol to give the compound of the formula XII

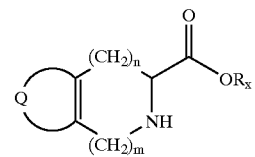

(XII)

where R$_x$ is (C$_1$–C$_4$)-alkyl or benzyl, or b) reacting a compound of the formula XII prepared according to process a) with the compound of the formula XIII

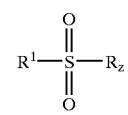

(XIII)

where R$^1$ is as defined in formula I and R$_Z$ is a chlorine atom, imidazolyl or —OH, in the presence of a base or, if appropriate, a dehydrating agent to give a compound of the formula XIV

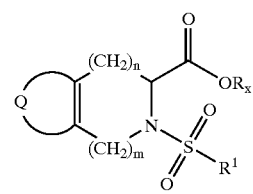

(XIV)

where Q, R$^1$, n and m are as defined in formula I and R$_x$ is as defined in formula XII, or c) reacting a compound of the formula XII prepared according to process a) with a base and subsequently with a compound of the formula XIII to give a compound of the formula XIV, or d) reacting a compound of the formula XI with a compound of the formula XIII to give a compound of the formula XV

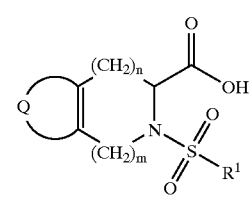

(XV)

where Q, R$^1$, n and m are as defined in formula I, or e) reacting a compound of the formula XIV to give a compound of the formula XV, or f) reacting a compound of the formula XIV prepared according to process b) or c) with the hydroxylamine of the formula XVI

   (XVI)

where $R_y$ is a hydrogen atom or a protective group for oxygen, to give the compound of the formula I and, if appropriate, removing the protective group for oxygen, or g) reacting a compound of the formula XV prepared according to process d) or e) with the hydroxylamine of the formula XVI to give the compound of the formula I, or h) separating into the pure enantiomers a compound of the formula I prepared according to process f) or g) which, owing to its chemical structure, exists in enantiomeric forms, by forming salts with enantiomerically pure acids or bases, chromatography using chiral stationary phases or derivatization by means of chiral enantiomerically pure compounds such as amino acids, separation of the resulting diastereomers, and removal of the chiral auxiliary, or i) isolating the compound of the formula I prepared according to processes f), g) or h) either in free form or, if acidic or basic groups are present, converting it, if appropriate, into physiologically tolerable salts.

In the case of the $(C_1$–$C_4)$-alcohols, the reaction according to process step a) is carried out under customary reaction conditions in the presence of HCl gas or thionyl chloride. The preparation of the corresponding benzyl esters of the formula XII is carried out in benzene or toluene using the appropriate alcohol and an acid such as p-toluenesulfonic acid. Tert-butyl esters can be prepared, for example, by known processes using isobutene and sulfuric acid.

The reaction according to process step b) is carried out in the presence of a basic compound such as N-methylmorpholine (NMM), N-ethylmorpholine (NEM), triethylamine (TEA), diisopropylethylamine (DIPEA), pyridine, collidine, imidazole or sodium carbonate in solvents such as tetrahydrofuran (THF), dimethylformamide (DMF), dimethylacetamide, dioxane, acetonitrile, toluene, chloroform or methylene chloride, or even in the presence of water. Preference is given to using the sulfonyl chlorides of the formula XIII in the presence of NMM in THF.

The reaction according to process step c) is carried out in the presence of a base such as KOH, LiOH or NaOH.

The reaction according to process step d) is carried out in an aqueous organic solvent system, preferably in THF and water in the presence of a base such as sodium carbonate and the compound of the formula XIII. Furthermore, the reaction can be carried out in the absence of solvent with or without base under reduced pressure, as obtained by use of an oil pump.

The hydrolysis of the compound of the formula XIV to give the compound of the formula XV (process step e) is carried out, for example, basic, preferably acidic or, in the case of the benzyl derivatives, by hydrogen-olysis. In the case of basic hydrolysis, it is necessary to free the carboxylic acid from the carboxylic acid salt by treatment with another acid, for example dilute hydrochloric acid.

The reaction according to process step f) is carried out under the conditions which are customary for the formation of carboxamides, in a suitable solvent, for example an alcohol or dimethylformamide.

For the reaction according to process step g), the carboxylic acids of the formula XV are activated. Activated carboxylic acids are, for example, acyl halides, acyl azides, mixed anhydrides and carbonates. Preference is given to acyl chlorides or fluorides, mixed anhydrides and carbonates of pivaloyl chloride, ethyl, isopropyl or isobutyl chloroformate; active esters such as cyanoethyl, o- or p-nitrophenyl, succinimido or phthalimido, and to the activated carboxylic acids which are obtainable using coupling reagents such as diisopropylcarbodiimide (DIC), carbonyldiimidazole (CDI), dicylo-hexylcarbodimide (DCC) or benzotriazolyltetramethyluronium tetrafluoro-borate (TBTU), if appropriate with addition of hydroxybenzotriazole (HObt) or oxohydroxybenzotriazine (HOObt), preferred solvents being aprotic solvents.

The starting materials and reagents employed can either be prepared by known processes, or they are commercially available.

Suitable imino acids of the formula XI where n and m are 1 its, for example, 1,2,3,4-tetrahydroisoquinoline-3-carboxylic acid, 1,2,3,4-tetrahydro-9H-pyrido(3,4-b)-indole-3-carboxylic acid or optionally 1- or 3-substituted 4,5,6,7-tetrahydro-1H-imidazo(4,5-c)-pyridine-6-carboxylic acids. They are preferably prepared by cyclizing the corresponding amino acids with formaldehyde in the presence of an acid such as hydrochloric acid or sulfuric acid using the method of Pictet-Spengler (see W. M. Whaley, Organic Reactions 6 (1951) 151.

In the case that in the imino acid of the formula XI n is zero and m is 2, it is possible to use, for example, 1,2,3,4-tetrahydro-9H-pyrido(3,4-b)indol-1-carboxylic acid and 6,7-propylene-1,2,3,4-tetraisoquinoline-1-carboxylic acid as starting material. To prepare the latter compound, indane is Friedel-Crafts alkylated with phenylsulfonylarziridine. The cyclization of the resulting 4-(2-benzenesulfonamidoethyl) indane is carried out using glyoxylic acid in HBr/glacial acetic acid; the subsequent cleavage of the benzenesulfonyl radical is carried out using iodine/red phosphorus in HBr/glacial acetic acid.

An example of the case where in the compound XI n is 1 and m is zero is indoline-2-carboxylic acid. It is prepared, for example, by catalytic hydrogenation of indol-2-carboxylic acid. Furthermore, mention may be made of the cyclization of 2-chlorophenylalanine or 2-hydroxy-3-(2-chlorophenyl)-propionic acid to give imino acids of the formula XI.

If compounds of the formula I permit diastereomeric or enantiomeric forms and are obtained as mixtures thereof in the synthesis chosen, separation into the pure stereoisomers is possible either by chromatography over an optionally chiral carrier material or, if the racemic compound of the formula I or a compound of the formula XI is capable of forming salts, by fractional crystallization of the diastereomeric salts formed with an optically active base or acid as auxiliary. Suitable chiral stationary phases for thin-layer- or column-chromatographic separation of enantiomers are, for example, modified silica carriers (Pirkle phases) and high-molecular-weight carbohydrates such as triacetylcellulose. For analytical purposes, gas-chromatographic methods using chiral stationary phases may also be used, after appropriate derivatization known to the person skilled in the art. The enantiomers of racemic carboxylic acids are separated using an optically active, usually commercially available base such as (–)-nicotine, (+)- and (–)-phenylethylamine, quinine bases, L-lysine or L- and D-arginine to form the diastereomeric salts, which differ in solubility. The less soluble component is isolated as a solid, the more soluble diastereomer is recovered from the mother liquor, and the pure enantiomers are obtained from the resulting diastereomeric salts. In basically the same manner, the racemic compounds of the formula I which contain a basic group such as an amino group can be converted into the pure enantiomers using optically active acids such as (+)-camphor-10-sulfonic acid, D- and L-tartaric acid, D- and L-lactic acid and (+) and (−)-mandelic acid. It is also possible to convert chiral compounds containing alcohol or amine functions into the corresponding esters or amides using appropriately activated or optionally n-protected enantiomerically pure amino acids, or, conversely, to convert chiral carboxylic acids into the amides using carboxyl-protected enantiomerically pure amino acids, or into the corresponding chiral esters using enantiomerically pure hydroxycarboxylic acids such as lactic acid. The chirality of the enantiomerically pure amino acid or alcohol radical can then be employed to separate the isomers by resolving the diastereomers that are now present using crystallization or chromatography over suitable stationary phases and then removing the chiral moiety which has been carried along by means of suitable methods.

Acidic or basic products of the compound of the formula I may be present in the form of their salts or in free form. Preference is given to pharmacologically tolerable salts, for example alkali metal or alkaline earth metal salts or hydrochlorides, hydrobromides, sulfates, hemisulfates, all possible phosphates and salts of the amino acids, natural, bases or carboxylic acids.

Hydroxylamine can be employed in free form, obtainable from hydroxylamine salts and a suitable base in solution or in O-protected form, or in each case also in the form of its salts. The preparation of free hydroxylamine is known from the literature and can be carried out, for example, in alcoholic solution. Preference is given to using the hydrochloride together with alkoxides such as Na methoxide, potassium hydroxide or potassium t-butoxide.

O-protected hydroxylamine derivatives preferably contain protective groups which can be removed under mild conditions. Particular preference is given here to protective groups of the silyl, benzyl and acetal types. Particularly suitable for this purpose are the O-trimethylsilyl, O-tert-butyldimethylsilyl, O-benzyl, O-tert-butyl and the O-tetrahydropyranyl derivative.

Starting materials and intermediates which are employed for preparing the compound of the formula I may, if they contain functional groups such as hydroxyl, thiole, amino or carboxyl, for example in the radicals $R^1$, $R^2$, $R^3$, $R^4$, $R^5$, $R^6$, $R^7$ and $R^8$, be employed in suitably protected form.

The introduction of protective groups is required in all those cases where, in a desired chemical reaction, undesirable side-reactions are to be expected at other locations than reaction centers (T. W. Greene, Protective Groups in Organic Synthesis, Wiley, New York, 1991).

The protective groups employed can be removed before or after the conversion of the compound of the formula XII into the compound of the formula I.

Particularly, suitable for use as auxiliaries and bases are: HObt, HOObt, N-hydroxysuccinamide (HOSu), TEA, NMM, NEM, DIPEA, imidazole. Preferred solvents for the reaction are: dichloromethane (DCM), THF, acetonitrile, N,N-dimethylacetamide (DMA), DMF and N-methylpyrrolidone (NMP).

The preferred temperatures are between −78° C. and +90° C., depending on the boiling point and the nature of the solvent used. Particular preference is given to the temperature range from −20 to +30° C.

The preparation of physiologically tolerable salts from compounds of the formula I which are capable of forming salts, including their stereoisomeric forms, is carried out in a manner known per se. The carboxylic acids and hydroxamic acids form stable alkali metal, alkaline earth metal or optionally substituted ammonium salts with basic reagents such as hydroxides, carbonates, bicarbonates, alkoxides and ammonia or organic bases, for example trimethyl- or triethylamine, ethanolamine or triethanolamine or else basic amino acids, for example lysine, ornithine or arginine. If the compounds of the formula I have basic groups, it is also possible to prepare stable acid addition salts by using strong acids. Suitable for this purpose are both inorganic and organic acids, such as hydrochloric, hydrobromic, sulfuric, phosphoric, methanesulfonic, benzenesulfonic, p-toluenesulfonic, 4-bromobenzenesulfonic, cyclohexylamidosulfonic, trifluoromethylsulfonic, acetic, oxalic, tartaric, succinic or trifluoroacetic acid.

The invention also relates to pharmaceuticals which contain an effective amount of at least one compound of the formula I and/or of a physiologically tolerable salt of the compound of the formula I and/or an optionally stereoisomeric form of the compound of the formula I, together with a pharmaceutically suitable and physiologically tolerable excipient, additive and/or other active compounds and auxiliaries.

On account of the pharmacological properties, the compounds according to the invention are suitable for the prophylaxis and therapy of all those disorders in the course of which is involved an increased activity of matrix-degrading metalloproteinases. These include degenerative joint disorders such as osteoarthroses, spondyloses, chondrolysis after joint traumas or relatively long immobilization of the joint after meniscus or patella injuries or tears of the ligaments. Furthermore, these also include disorders of the connective tissue such as collagenoses, periodontal disorders, wound healing disorders and chronic disorders of the locomotory apparatus such as inflammatory, immunologically or metabolically related acute and chronic arthritides, arthropathies, myalgias and disorders of the bone metabolism. The compounds of the formula I are also suitable for the treatment of ulceration, atherosclerosis and stenoses. The compounds of the formula I furthermore suppress the release of the cellular tumor necrosis factor (TNFα) to a considerable extent and are therefore suitable for the treatment of inflammations, carcinomatous disorders, formation of tumor metastases, cachexia, anorexia and septic shock.

The pharmaceuticals according to the invention are in general administered orally or parenterally. Rectal or transdermal administration is also possible.

The invention also relates to a process for the production of a pharmaceutical, which comprises bringing at least one compound of the formula I into a suitable administration form using a pharmaceutically suitable and physiologically tolerable excipient and, if appropriate, other suitable active compounds, additives or auxiliaries.

Suitable solid pharmaceutical preparation forms are, for example, granules, powders, coated tablets, tablets, (micro) capsules, suppositories, syrups, juices, suspensions, emulsions, drops or injectable solutions and also preparations with protracted release of active compound, in whose preparation customary auxiliaries, such as excipients, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactoprotein, gelatin, starch, cellulose and its derivatives, animal and vegetable oils such as fish liver oil, sunflower, groundnut or sesame oil, polyethylene glycol and solvents such as, for example, sterile water and mono- or polyhydric alcohols such as glycerol.

The pharmaceutical preparations are preferably prepared and administered in dose units, each unit as active constituent containing a specific dose of the compound of the formula I according to the invention. In solid dose units such as tablets, capsules, coated tablets or suppositories, this dose can be up to approximately 1000 mg, but preferably approximately 50 to 300 mg, and in injection solutions in ampoule form up to approximately 300 mg, preferably approximately 10 to 100 mg.

For the treatment of an adult patient weighing approximately 70 kg—depending on the efficacy of the compounds according to formula I, daily doses of approximately 20 mg to 1000 mg of active compound, preferably approximately 100 mg to 560 mg, are indicated. Under certain circumstances, however, higher or lower daily doses may be appropriate. The daily dose can be administered both by single administration in the form of an individual dose unit or else of several smaller dose units and by multiple administration of subdivided doses at specific initervals.

$^1$H-NMR spectra have been recorded on a 200 MHz apparatus from Varian, in general using tetramethylsilane (TMS) as an internal standard and at room temperature (RT). The solvents used are indicated in each case. Generally, final products are determined by mass spectroscopic methods (FAB-, ESI-MS). Temperature data in degrees Celsius, RT means room temperature (22° C.–26° C.). Abbreviations used are either explained or correspond to the customary conventions.

PREPARATION EXAMPLES

The preparation of the compounds 1–12, 14–23, 27, 30 and 33 in Table 1 was carried out similarly to the procedures given in Examples 13, 24–26, 28, 29, 31 and 32.

In Examples 4 to 9, a sulfonation was initially carried out, using p-(Ex. 4, 6, 9) or m-(Ex. 5,7,8) nitrobenzenesulfonyl chloride as described under "Tic-sulfonation" (see Example 13). Subsequently, the hydrogenation of the nitro group was carried out under standard conditions known to the person skilled in the art, using hydrogen under atmospheric pressure and 10% Pd on activated carbon in methanol to give the amine.

In all cases, it is also possible to employ the Tic benzyl ester described under Example 13 for the sulfonation. In the subsequent hydrogenation, cleavage of the benzyl ester and reduction to give the amine occur simultaneously. The identical products which are obtained in both cases, p- or m-aminobenzenesulfonyl Tic are subsequently reacted further as follows:

Example 4

Initially, acetylation under standard conditions (triethylamine/DMAP/acetic anhydride) is carried out; the N-acetyl compound, which is obtained in good yield, is subsequently reacted further to give the hydroxamic acid, as described in Example 25.

Examples 5 and 6

To prepare the hydroxamic acid, the p-aminobenzenesulfonyl-Tic is activated in the same manner as described in Example 13, except that double the amount of ethyl chloroformate and N-methylmorpholine is employed. Irreversible N-ethoxycarbonylation takes place in one step, together with the activation of the carboxylic acid.

Examples 7, 8 and 9

The p- or m-aminobenzenesulfonyl-Tic described above is acylated under the Schotten-Baumann conditions known to the person skilled in the art. For this purpose, use is made of: Ex. 7: salicyloyl chloride, Example 8: p-methoxybenzoyl chloride, Example 9: benzyl chloroformate. The further reaction to give the hydroxamic acid is carried out as described in Example 25.

Example 13

R-2-(4-phenoxybenzenesulfonyl)-1,2,3,4-tetrahydroisoquinoline-3-hydroxamic acid

General Procedure:
Tic Benzyl Ester p-toluenesulfonate 1 mol of Tic (free amino acid), 10 moles of benzyl alcohol and 1 mol of p-toluenesulfonic acid monohydrate are dissolved or suspended in 1.2 l of toluene and heated under reflux using a water separator. After the reaction has ended, the solvent is evaporated and the solid crystalline residue is repeatedly taken up in diethyl ether and filtered off with suction and subsequently dried using oil pump vacuum. Yield: quantitative.

$^1$H NMR: (200 MHz, $\delta$ in ppm, DMSO-$d_6$) 9.7 (s, brd:, 2 H, prot.NH), 7.5–7.25 (2 m, 7H, arom.), 7.1 (d, 2H, arom. p-TsOH), 5.3 (s, 2H, $CH_2$ benzyl); 4.7 (dd, 1H, CHα); 4.4 "d", 2H, $CH_2$); 3.4–3.1 (m, 2H, $CH_2$); 2.3 (s, 1H, $CH_3$ p-TsOH).

Tic Sulfonation

At 0° C., 0.1 mol of Tic solution (free amino acid 17.7 g) in 50 ml of 2 N aqueous NaOH is admixed with finely powdered sulfonyl chloride (105 mmol), followed by 14.2 g (110 mmol) of diisopropylethylamine and 50 ml of acetone or THF. The ice bath is removed after 10 min and the more or less homogeneous solution is stirred at RT for a further 6 h. The reaction mixture is subsequently concentrated, admixed with 300 ml of ethyl acetate and acidified with 4 N HCl. The organic phase is separated off and the aqueous phase is extracted two more times with in each case 50 ml of ethyl acetate. The combined organic phases are extracted with saturated NaCl solution and dried over sodium sulfate. The solvent is distilled off and the sulfonated tetrahydroisoquinolinecarboxylic acid remains as an oily or solid residue which in some cases may be purified by recrystallization from ethyl acetate/petroleum ether, but which frequently is sufficiently pure for further reaction.

13a Methyl R-2-(4-phenoxybenzenesulfonyl)-1,2,3,4-tetrahydroisoquinoline-3-carboxylate A solution of 1.92 g (0.01 mol) of methyl R-1,2,3,4-tetrahydroisoquinoline-3-carboxylate and 2.7 g (0.01 mol) of 4-phenoxybenzenesulfonyl chloride in 50 ml of absolute THF are heated under reflux in the presence of 1.7 ml (0.01 mol) of N-ethylmorpholine for 8 h. The solvent is removed, the residue is taken up in dichloromethane and the solution is extracted successively with 5% citric acid, 5% sodium bicarbonate solution and 2× with water. The organic phase is dried over sodium sulfate and concentrated to give the ester which is subjected to further reactions without purification.

Yield: 4.0 g (95% of theory) of 13a.

13b R-2-(4-phenoxybenzenesulfonyl)-1,2,3,4-tetrahydroisoquinoline-3-carboxylic acid At room temperature, a solution of 4.0 g (9.5 mmol) of the ester (13a) in 50 ml of isopropanol is stirred after addition of 9.5 ml of 1 N aqueous sodium hydroxide solution for 24 h. The mixture is then acidified with 1 N hydrochloric acid and evaporated to dryness under reduced pressure. The residue is taken up in toluene, the solution is extracted with 5% citric acid and the organic phase is dried over sodium sulfate and concentrated under reduced pressure.

Yield: 3.4 g of carboxylic acid 13b (83% of theory).

Melting point: 147° C.

13c R-2-(4-phenoxybenzenesulfonyl)-1,2,3,4-tetrahydroisoquinoline-3-hydroxamic acid 3.4 g (8.3 mmol) of the carboxylic acid 13b are dissolved in 30 ml of DMF and, at −20° C., admixed successively with 1.4 g (12 mmol) of N-ethyl-morpholine and 1.13 g (8.3 mmol) of isobutyl chloroformate. After an activation time of 30 min, the mixture is admixed with 4.37 g (41.5 mmol) of O-trimethylsilylhydroxylamine and stirred at room temperature for a further 4 h. 250 ml of ethyl acetate and 500 ml of water are added to the mixture which is then acidified with citric acid. The organic phase is separated off and the aqueous phase is extracted 4×, and the combined organic phases are dried over sodium sulfate and concentrated under reduced pressure. Recrystallization from toluene/ethyl acetate (1:1) affords the title compound 13.

Yield: 2.9 g (82% of theory) Melting point: 170° C. (decomposition).

Example 17

Trans-beta-styrenesulfonyl chloride is employed for the sulfonation of the Tic benzyl ester under standard conditions (see Example 13). In the subsequent hydrogenation (H2, Pd/C), debenzylation and hydrogenation of the double bond are effected in one step. Subsequently formation of the hydroxamic acid by the method of Example 25.

Examples 20, 21 and 22

The starting material is commercially available 7-hydroxy-Tic. This is sulfonated under standard conditions according to process variant d). This gives, after customary work-up, a mixture of 2- and 7-disulfonated and exclusively 2-sulfonated 7-hydroxy-Tic. However, at this stage it is not necessary to separate the two compounds. Direct further conversion to give the hydroxamic acid is carried out under standard conditions. As expected, partial ethoxycarbonylation of the 7-hydroxyl group takes place during the activation. The hydroxamic acid product mixture therefore contains all three products which can be separated by chromatography over silica gel 60, preparative thin-layer chromatography or HPLC.

Example 23

The starting material for the preparation of 7-nitro-Tic is enantiomerically pure commercial (R)-Tic-OH or (S)-Tic-OH. The 7-nitro-Tic is prepared according to E. D. Bergann, J. Am. Chem. Soc. 74, 4947 (1952) or according to E. Erlenmever, A. Lipp, Liebigs Ann. Chem. 219, 218 (1983) by nitration with nitrating acid. A mixture of the 6- and 7-nitro isomers is formed, and the reaction mixture additionally contains unnitrated starting materials. Prior to the separation, the mixture is initially sulfonated under standard conditions. The resulting mixture of the three sulfonamides can then be chromatographed over silica gel 60. Successively, mixed fractions containing educt/6-nitro- and 6-nitro-/7-nitro-(4-methoxybenzenesulfonyl)-Tic are obtained; finally, fractions of pure 7-nitro compound are eluted. This can be further converted into the hydroxamic acid, in a customary manner similar to Example 25.

Example 24
2-(4-Methoxybenzenesulfonyl)-6,7-methylenedioxy-1,2,3,4-tetrahydroisoquinoline-3-hydroxamic acid The preparation of the corresponding benzyl carboxylate from the carboxylic acid corresponds to the general procedure (see Example 13). Sulfonation or benzyl ester cleavage is carried out similarly to Example 25a. The reaction of the free sulfonated carboxylic acid is carried out as described under 25b.

After treatment with diethyl ether, the product is obtained in crystalline form. Yield: 140 mg, 57% of theory; melting point 166° C.

Example 25
2-(4-Methoxybenzenesulfonyl)-6,7,8-trimethoxy-1,2,3,4-tetrahydroisoquinoline-3-hydroxamic acid 25a 2-(4-Methoxybenzenesulfonyl)-6,7,8-trimethoxy-1,2,3,4-tetrahydroisoquinoline-3-carboxylic acid The preparation of the benzyl ester is carried out according to the general procedure (see Example 13). For the sulfonation, 1.2 g (3.05 mmol) of the benzyl ester are employed. This is dissolved in 20 ml of THF and, at 0° C., admixed with 0.63 g (3.05 mmol) of 4-methoxybenzenesulfonyl chloride. 0.32 ml of N-methylmorpholine are added and the reaction mixture is stirred at 0° C. to room temperature overnight. The mixture is subsequently admixed with 20 ml of ethyl acetate and extracted with 10% strength sodium carbonate solution and saturated NaCl solution. The organic phase is dried over sodium sulfate, filtered and concentrated under reduced pressure. The residue that remains is subjected to chromatography under pressure over silica gel 60 using ethyl acetate/petroleum ester/glacial acetic acid 20/10/1. Pure product fractions (600 mg) are combined and, after concentration, directly hydrogenated using 100 mg of 10% Pd/C in 50 ml of ethanol. After the reaction has ended, the catalyst is separated off and the remaining solution is concentrated under reduced pressure. This gives 330 mg (66% of theory).

25b 2-(4-Methoxybenzenesulfonyl)-6,7,8-trimethoxy-1,2,3,4-tetrahydroisoquinoline-3-hydroxamic acid 330 mg (0.75 mmol) of the carboxylic acid from Example 25a are dissolved in 15 ml of THF and, at −20° C., admixed successively with 0.07 ml (0.75 mmol) of ethyl chloroformate and 0.15 ml (1.5 mmol) of N-methylmorpholine (NMM). After 30 min at this temperature, the mixture is mixed with 0.474 ml of O-trimethylsilylhydroxylamine (3.75 mmol). After 6 h at RT, 30 ml of ethyl acetate are added to the mixture which is then extracted with 20% strength aqueous citric acid and saturated NaCl solution. The organic phase is dried over sodium sulfate and concentrated under reduced pressure, leaving 290 mg of a clear viscous oil which crystallizes on treatment with diethyl ether.

Example 26
2-(Morpholinosulfonyl)-1,2,3,4-tetrahydroisoquinoline-3-hydroxamic acid 26a Methyl 2-(morpholinosulfonyl)-1,2,3,4-tetrahydroisoquinoline-3-carboxylate With stirring, 4.2 g (0.025 mol) of morpholine-N-sulfonyl chloride in 20 ml of THF are added dropwise to a solution of 4.8 g (0.025 mol) of methyl 1,2,3,4-tetrahydroisoquinoline-3-carboxylate and 2.9 g (0.025 mol) of N-ethylmorpholine. The mixture is stirred at RT for 2 h and then heated under reflux for another 2 h so that the reaction goes to completion. $CHCl_3$ is added to the reaction solution, which is then treated with 5% strength citric acid, 5% strength $NaHCO_3$ solution and water. The organic phase is dried over $Na_2SO_4$ and evaporated to dryness. Yield of ester (26a): 7.5 g (92% of theory)

26b 2-(Morpholinosulfonyl)-1,2,3,4-tetrahydroisoquinoline-3-carboxylic acid

Reaction of 7.5 g (0.023 mol) of 26a by the method of 13b.

Yield of carboxylic acid 26b: 6.7 g (93% of theory).

26c 2-(Morpholinosulfonyl)-1,2,3,4-tetrahydroisoquinoline-3-hydroxamic acid 2.3 g (7.5 mmol) of the carboxylic acid 26b are dissolved in 40 ml of absolute THF and, at −20° C., admixed successively with 1.2 g (12 mmol) of N-methylmorpholine and 1.1 g (7.5 mmol) of isobutyl chloroformate. After 30 min, the mixture is admixed with 3.9 g (37.5 mmol) of O-trimethylsilylhydroxylamine and stirred at RT for a further 5 h. 200 ml of water are added and the mixture is acidified with dilute HCl and extracted repeatedly with dichloromethane. The pooled organic phases are dried over $Na_2SO_4$ and concentrated under reduced pressure. The resulting oil is chromatographed under pressure over silica gel 60 using ethyl acetate/dichloromethane (1:1) as mobile phase. Recrystallization of the product fractions from ethyl acetate gave crystalline hydroxamic acid 26c.

Yield: 1.4 g (55% of theory) Melting point: 164–165° C. (decomposition).

Example 28

1-(4-Methoxybenzenesulfonyl)indoline-2-hydroxamic acid 28a 1-(4-Methoxybenzenesulfonyl)indoline-2-carboxylic acid At 50° C. and 0.02 mbar, 1 g (6.1 mmol) of indoline-2-carboxylic acid and 2.5 g (12.2 mmol) of 4-methoxybenzenesulfonyl chloride are kept for 4 hours (h) in a kugelrohr which is rotated slowly and continuously. The brown crystalline product is subsequently taken up in sodium carbonate solution and extracted twice with diethyl ether. The aqueous phase is acidified using 6 N HCl and extracted four times with ethyl acetate. The combined organic phases are extracted with saturated NaCl solution, dried over sodium sulfate and concentrated under reduced pressure. Residual solvent is removed using oil pump vacuum.

Yield: 1.34 g, (65% of theory).

$^1$H-NMR: (DMSO-$d_6$) 7.8; 7.1 (2d, 4H, arom. p-TsOH); 7.4–7.0 (m, 4H, arom.); 4.9 (dd, 1H, CHα); 3.8 (2, 3H, OMe); 3.4–2.9 (2 dd, 2H, $CH_2$).

28b 1-(4-Methoxybenzenesulfonyl)indoline-2-hydroxamic acid 1.3 g (3.9 mmol) of the 1-(4-methoxybenzenesulfonyl) indoline-2-carboxylic acid of Example 28a are dissolved in 10 ml of N,N-dimethylacetamide (DMA) and, at −20° C., admixed successively with 0.37 ml (1 equivalent) of ethyl chloroformate and 0.81 ml of N-methylmorpholine. After an activation time of 30 minutes (min), the mixture is admixed with 3.8 ml (19.5 mmol) of O-trimethylsilylhydroxylamine and stirred at RT for a further 4 h. The mixture is diluted with ethyl acetate, acidified with citric acid and, after removal of the aqueous phase, washed with saturated NaCl solution. The organic phase is dried over sodium sulfate, filtered off and concentrated under reduced pressure. The resulting oil is subjected to chromatography under pressure over silica gel 60 using dichloromethane/ethyl acetate/acetic acid 5.5/3.5/1 as mobile phase. Product fractions (showing positive iron (III) chloride-reaction) are pooled and concentrated. The crystalline product is subsequently admixed with diethyl ether and freed of residual solvent under reduced pressure.

Yield: 400 mg (33% of theory) Melting point: 142° C.

Example 29

R-5-(4-methoxybenzenesulfonyl)-4,5,6,7-tetrahydro-1H-imidazo-(4,5-c)-pyridine-6-hydroxamic acid hydrochloride 29a: R-3,5-di(4-methoxybenzenesulfonyl)-4,5,6,7-tetrahydro-1H-imidazo-(4,5-c)-pyridine-6-carboxylic acid With ice-cooling, 15 ml of 2 N NaOH and 4.5 g (42 mmol) of sodium carbonate are added successively to a solution of 6.1 g (30 mmol) of 4,5,6,7-tetrahydro-1H-imidazo-(4,5-c)-pyridine-6-carboxylic acid hydrochloride in 50 ml of water. With stirring, 13.7 g (67 mmol) of 4-methoxybenzenesulfonyl chloride in 40 ml of ether are added. The reaction mixture is stirred at RT for a further 24 hours and then with ice-cooling adjusted to pH 3–4 using 5 N HCl and extracted with ethyl acetate. The organic phase is dried over sodium sulfate, filtered and concentrated to dryness to give 11.9 g (78% of theory) of the desired product in the form of an oil.

29b: R-5-(4-methoxybenzenesulfonyl)-4,5,6,7-tetrahydro-1H-imidazo-(4,5-c)-pyridine-6-carboxylic acid hydrochloride With ice-cooling and stirring, 23.5 ml each of a 1 N NaOH solution are added dropwise in intervals of 1 hour to a solution of 11.0 g (24 mmol) of disulfonated intermediate in 300 ml of methanol. After 6 hours, a final 15 ml of 1 NaOH are added and the mixture is stirred at RT overnight. The methanol is removed under reduced pressure and the mixture is then adjusted to pH 5 using 5 N HCl. The precipitated crystals are filtered off with suction and dried under reduced pressure over P2O5.

Yield: 5.2 g (60% of theory) of 29b.

Melting point: 264–265° C. (decomp.).

29c: R-5-(4-methoxybenzenesulfonyl)-4,5,6,7-tetrahydro-1H-imidazo-(4,5-c)-pyridine-6-hydroxamic acid hydrochloride 8.0 g (24 mmol) of compound 29b in 60 ml of DMF are admixed with 4.27 g (24 mmol) of tetramethylammonium hydroxide and then, at 0° C., with 2.7 g (24 mmol) of N-ethylmorpholine and, a little at a time, with 5.2 g (24 mmol) of di-tert-butyl dicarbonate. The reaction mixture is stirred overnight, poured onto ice-water, adjusted to pH 5 using dilute HCl and extracted repeatedly with ethyl acetate. After removal of the solvent, the combined dried organic phase affords 10.5 g of BOC-protected 29b which is used directly for preparing the hydroxamic acid.

To this end, 10.5 g (23 mmol) of the above compound are dissolved in 150 ml of absolute THF and, at −20° C., admixed with 4.4 g (38 mmol) of N-ethylmorpholine and 3.4 g (25 mmol) of isobutyl chloroformate. The mixture is stirred for 1 hour, after which 10.9 g (0.1 mol) of O-trimethylsilylhydroxylamine are added, the temperature being kept at −20° C. for 1 hour. After a further 4 hours of stirring at RT, the reaction mixture is adjusted to pH=1 using 1N HCl, admixed with 300 ml of water and extracted repeatedly with dichloromethane. The combined organic phases are dried over sodium sulfate and concentrated to dryness under reduced pressure.

To cleave the BOC protective group, 8.1 g of the remaining oil are taken up in 50 ml of dichloromethane and 25 ml of trifluoroacetic acid are added dropwise at 0° C. The reaction mixture is stirred at RT for 4 hours and then concentrated under reduced pressure. The residue is digested with dichloromethane and then dissolved in 0.1 N HCl, filtered and freeze-dried.

Yield of hydroxamic acid 29: 5.2 g (56% of theory).

Melting point: 110° C.

Example 31
R-2-(4-methoxybenzenesulfonyl)-1,2,3,4-tetrahydro-9H-pyrido-(3,4-b)-indole-3-hydroxamic acid 31a R-2-(4-methoxybenzenesulfonyl)-1,2,3,4-tetrahydro-9H-pyrido-(3,4-b)-indole-3carboxylic acid A solution of 2.16 g (10 mmol) of 1,2,3,4-tetrahydro-9H-pyrido(3,4-b)-indole-3-carboxylic acid in a mixture of 10 ml of acetone and 10 ml of water is, after addition of 10.5 ml of 2 N NaOH, admixed with stirring with 2.06 g (10 mmol) of 4-methoxybenzenesulfonyl chloride. The solution is stirred at room temperature for 18 hours, the acetone is removed and the pH is adjusted to 1 using concentrated HCl. The resulting precipitate is filtered off, washed with water and dried.

Yield: 2.7 g of carboxylic acid 31a (85% of theory).
Melting point: 232–234° C.

31b R-2-(4-methoxybenzenesulfonyl)-1,2,3,4-tetrahydro-9H-pyrido(3,4-b)-indole-3-hydroxamic acid 2.5 g (7.4 mmol) of the carboxylic acid 31a, are dissolved in 40 ml of absolute DMF and, at −20° C., admixed successively with 1.4 ml (12 mmol) of N-ethylmorpholine and 0.97 ml (7.4 mmol) of isobutyl chloroformate. After an activation time of 30 min, 4.53 ml (37 mmol) of O-trimethylsilylhydroxylamine are added arid the mixture is subsequently stirred at room temperature for 19 hours. The mixture is adjusted to pH=3.5 using citric acid and then extracted repeatedly with ethyl acetate. The combined organic phases are dried over sodium sulfate, concentrated under reduced pressure and purified by silica gel chromatography using methylene chloride/methanol (95:5).

Yield: 2.4 g of hydroxamic acid (91.5% of theory).
Melting point: 87° C.

Example 32
R-2-(4-phenoxybenzenesulfonyl)-1,2,3,4-tetrahydro-9H-pyrido(3,4-b)-indole-3-hydroxamic acid Preparation by the Method of Example 31
Melting point: 110–111° C.

Example 33
R-2-(4-morpholinobenzenesulfonyl)-1,2,3,4-tetrahydro-9H-pyrido(3,4-b)-indole-3-hydroxamic acid Preparation by the Method of Example 31
Melting point: 125° C. (decomposition).

Example 42
R-2-[4-(4-chlorophenoxy)benzenesulfonyl]-1,2,3,4-tetrahydroisoquinoline-3-carboxylic acid 8.2 g (46.4 mmol) of R-1,2,3,4-tetrahydroisoquinoline-3-carboxylic acid are admixed with 46.4 ml of 1N NaOH and 50 ml of acetone and dissolved in water. At −5° C. and with stirring, 14.1 g (46.4 mmol) of 4-(4-chlorophenyloxy) benzenesulfonyl chloride in 50 ml of THF are added dropwise and, after half has been added, the reaction mixture is admixed with 0.6 g (46.4 mmol) of diisopropylethylamine. The mixture is stirred overnight, the precipitate is filtered off and the filtrate is adjusted to pH=3 using 2 N HCl and extracted repeatedly with dichloromethane. The combined organic phases are dried over sodium sulfate, filtered and evaporated to dryness under reduced pressure. Recrystallization from toluene and drying under reduced pressure gives the title compound.

Yield: 16.1 g (78% of theory) Melting point: 168–169° C.

TABLE 1

Hydroxamic acids of the formula I

| Example No. | Structure | | mp (° C.) | Solvent | $^1$H NMR |
|---|---|---|---|---|---|
| 1 | (structure) | | | DMSO-d6 | 2.7–3.1(m, 2H)4–4.7(2m, 2H) 7–7.8(3m, 9H)9.5; 10.6(2s, br, 2H) |
| 2 | (structure) | chiral | 94 Decomp. | CDCL3 | 2.65–2.8(m, 1H); 3.1–3.25(m, 1H); 4.35–4.75(m, 3H); 6.9–7.2(m, 4H); 7.3–7.65(m, 7H); 7.8(d, 2H) |

TABLE 1-continued
Hydroxamic acids of the formula I
| Example No. | Structure | mp (° C.) | Solvent | ¹H NMR |
|---|---|---|---|---|
| 3 | 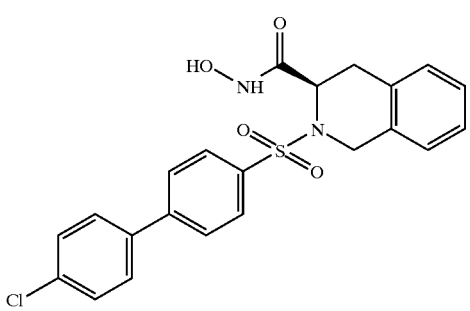 | | DMSO-d6 | 2.9(m, 2H); 4.5(t, 1H); 4.6(m, 2H); 7.0–7.9(m 12H); 9.9(s, 1H); 10.8(s, 1H) |
| 4 | 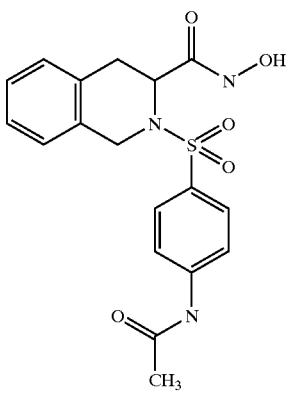 | | DMSO-d6 | 2.1(s, 3H)2.8–3.5(2m; 2H), 4.3–4.6(m, 3H)7.1; 7.7(2m, 8H)8.65; 8.85; 10.3; 10.8(4s, 2h) |
| 5 | 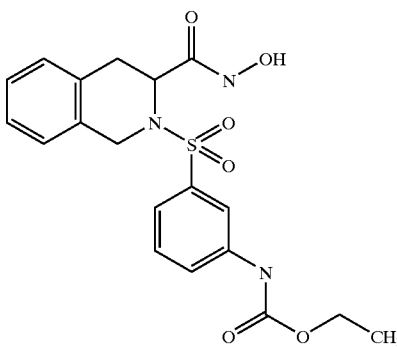 | | DMSO-d6 | 1.2(t, 3H)2.85(m, brd, 2H)4.15 (q, 2H)4.4–4.7(m, 3H)7.1(m, brd, 4H)7.4(m, 2H)7.6(m, 2H)8; 9.9; 10.7(3s, 3H) |
| 6 | 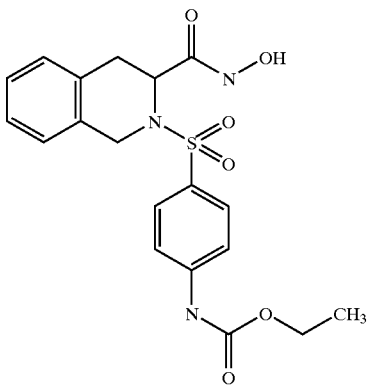 | | DMSO-d6 | 1.2(t, 3H)2.8(m, brd, 2H)4.15(d, 2H)4.3–4.6(m, 3H)7.1(m, brd, 4H)7.55; 7.7(2d, 4H)8.7; 9.5(2s, 3H) |

TABLE 1-continued

Hydroxamic acids of the formula I

| Example No. | Structure | mp (° C.) | Solvent | ¹H NMR |
|---|---|---|---|---|
| 7 | 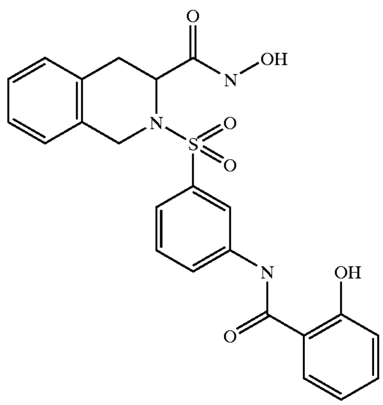 | | DMSO-d6 | 2(s, 3H)2.9(m, 2H)4.4–4.6(2m, 3H)7.1; 7.5; 7.9; 8.3(4m, 14H) |
| 8 | 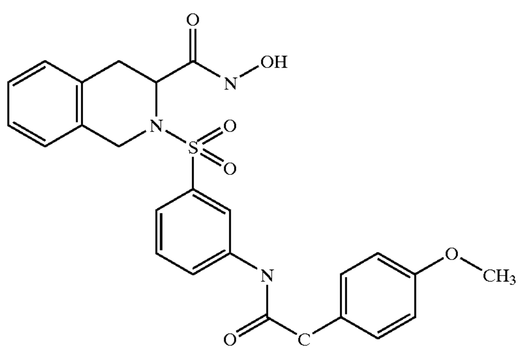 | | DMSO-d6 | 2.85(m, 2H)3.85(s, 3H)4.4–4.7 (2m, 3H)7.1; 7.4; 7.6; 8(4m, 13H)8.9; 10.8(2s, 2H) |
| 9 | chiral | | DMSO-d6 | 3(m, 2H)4.4–4.8(m, 3H)5.2(s, 3H)7.1–7.5(2m, 9H)7.55; 7.8 (2d, 4H)8.8; 10.7(2s, 2H) |
| 10 | chiral | 175 Decomp. | DMSO-d6 | 2.7–3.0(m, 2H); 3.25(m, 4H); 3.75(m, 4H); 4.45(t, 1H); 4.5(M, 2H); 6.9–7.65(m, 8H) |

TABLE 1-continued

Hydroxamic acids of the formula I

| Example No. | Structure | mp (° C.) | Solvent | $^1$H NMR |
|---|---|---|---|---|
| 11 | 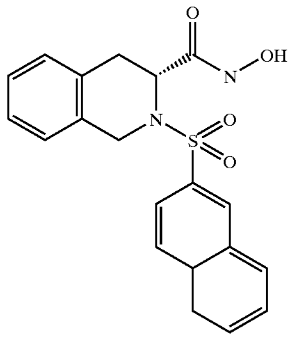 | chiral | DMSO-d6 | 2.7–3.1(m, 2H)4.5–4.8(m, 3H) 6.8–7.2(m, 4H)7.7(m, 3H)7.9– 8.2(m, 3H)8.5(s, 1H) |
| 12 | 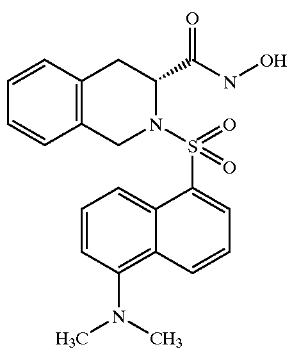 | chiral | DMSO-d6 | 2.8(s, 6H)2.95(d, brd, 2H)4.4– 4.8(m, 3H)7.1(m, 4H)7.25(d, 1H)7.6(dd, 2H)8.2("t", 2H)8.5 (d, 1H)8.9; 10.7(2s, 2H) |
| 13c | 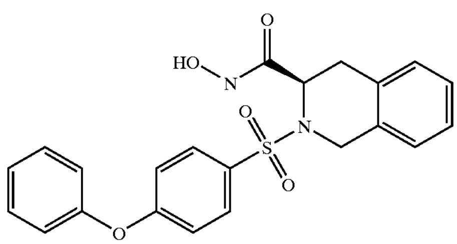 | 170 Decomp. | DMSO-d6 | 2.9(d, 2H); 4.4(m, 2H); 4.5(d, 1H); 6.9–7.95(m, 13H); 8.9(s, 1H); 10.75(s, 1H); |
| 14 | 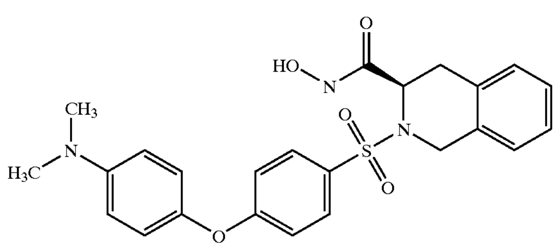 | chiral | DMSO-d6 | 2.9(m, 2H); 3.64(s 6H); 4.38(t, 1H); 4.5(m, 2H); 6.75–7.75(m, 12H); |
| 15 | 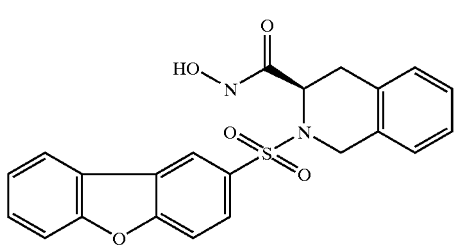 | chiral | DMSO-d6 | 2.85(m, 2H); 4.45(t, 1H); 4.63 (m, 2H); 6.9–8.7(m, 11H); 9.9(s, 1H); 10.8(s, 1H); |

TABLE 1-continued
Hydroxamic acids of the formula I
| Example No. | Structure | mp (° C.) | Solvent | ¹H NMR |
|---|---|---|---|---|
| 16 | 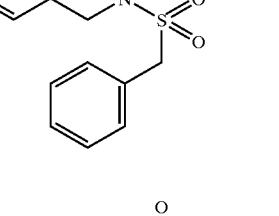 chiral | | DMSO-d6 | 2.9–3.1(m, 2H)3.9–4.6(2m, 5H) 7.15(m, 4H)7.3(m, 5H)8.85; 10.6(2s, 2H) |
| 17 | 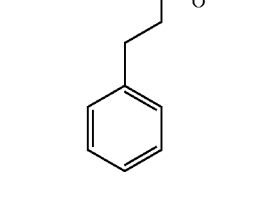 | | DMSO-d6 | 2.8–3.6(m, 6H)4.5–4.7(m, 3H) 7.1–7.4(m, 9H)8.7; 8.9; 9.5; 10.7(4s, 2H) |
| 18 | 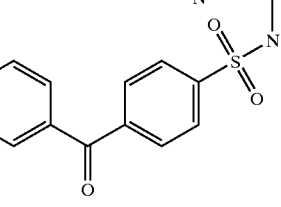 chiral | | DMSO-d6 | 2.95(m, 2H); 4.5(t 1H); 4.62(m 2H); 7.0–8.05(m, 13H); |
| 19 | 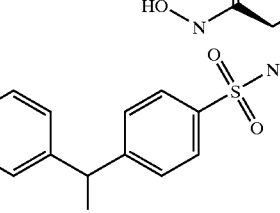 chiral | | DMSO-d6 | 2.85(m, 2H); 4.4(M, 1H); 4.53 (m, 2H); 6.95–7.8(M; 13H); |

TABLE 1-continued
Hydroxamic acids of the formula I
| Example No. | Structure | mp (° C.) | Solvent | ¹H NMR |
|---|---|---|---|---|
| 20 | 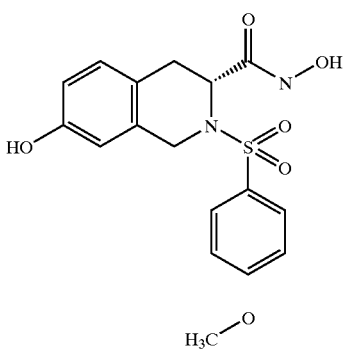 chiral | | DMSO-d6 | 2.8(m, 2H)3.8(s, 3H)4.35–4.6 (m, 3H)6.9–7.2; 7.6–7.8(2m; 7H)8.9; 10.8(2s, 2H) |
| 21 |  chiral | | DMSO-d6 | 1.3(t, 3H)2.85(m, 2H)3.8(s, 3H) 4.0–4.6(m, 5H)6.9–7.1; 7.6–7.8(2m, 7H)8.8; 10.8(2s, 2H) |
| 22 | 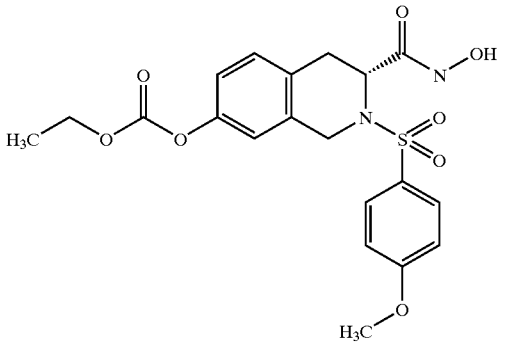 chiral | | DMSO-d6 | 2.8(m, 2H)3.8(s, 3H)3.9(s, 3H) 4.35–4.6(m, 3H)6.9–7.2; 7.6–7.8(2m, 11H)8.9; 10.9(2s, 2H) |
| 23 | 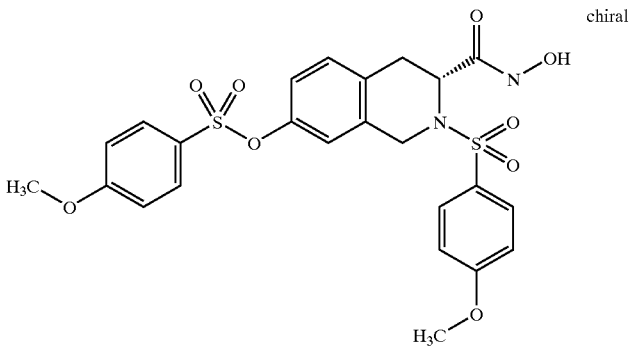 | | DMSO-d6 | 3.0(m, 2H)3.8(s, 3H)4.4–4.8(m, 3H)6.95; 7.7(2d, 4H)7.4(d, 1H) 7.95(dd, 1H)8.05(d, 1H)8.95; 10.8(2s, 2H) |

TABLE 1-continued

Hydroxamic acids of the formula I

| Example No. | Structure | mp (° C.) | Solvent | ¹H NMR |
|---|---|---|---|---|
| 24 | 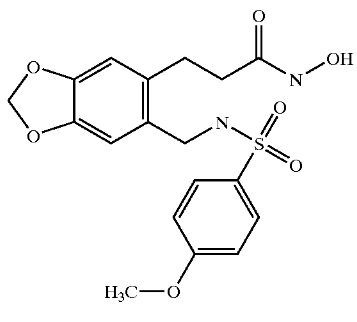 | 166 | DMSO-d6 | 2.7(m, 2H)3.8(s, 3H)4.2–4.5(m, 3H)5.9; 6.7; 7.0; 7.7(4d, 6H) 8.85; 10.7(2s, 2H) |
| 25 | 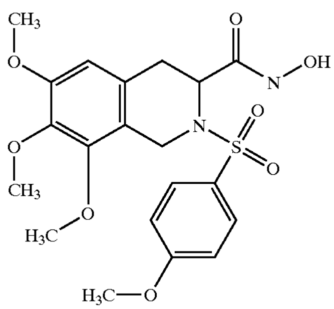 | | DMSO-d6 | 2.8(m, 2H)3.65–3.85(4s, 12H) 4.3–4.5(m, 3H)6.5(s, 1H)7.0; 7.7(2d, 4H)8.8; 10.7(2s, 2H) |
| 26 | 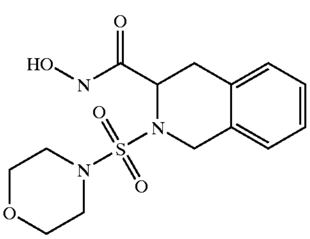 | 165 | DMSO-d6 | 2.9–3.35(m, 6H); 3.45–3.65(m, 4H); 4.38(m, 1H); 4.5; 4.65(AB, 2H); 7.2(s, 4H); 8.9(s, 1H); 10.65(s, 1H) |
| 27 | 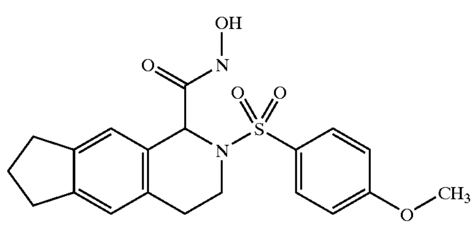 | | DMSO-d6 | 1.95(m, 2H); 2.5–2.95(m, 7H); 3.4(m, 1H); 3.8(s, 3H); 3.8–4.1 (m, 1H); 6.9–7.1(m, 4H); 7.7(d, 2H); 9.0–11.1(2s, 2H); |
| 28 | 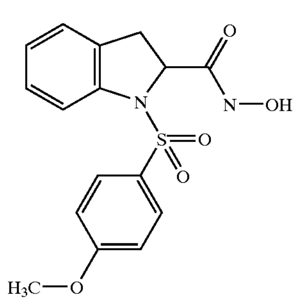 | 142 | DMSO-d6 | 2.8–3.2(m, 2H)3.8(s, 3H)4.6(dd 1H)7.0–7.8(3m, 8H)9.1; 10.9(2s 2H) |

TABLE 2

Carboxylic acids of the formula I

| Ex. | Structure | mp. (° C.) | ¹H NMR |
|---|---|---|---|
| 34 | chiral | 205 | (in CDCl3): 3.0–3.25(m, 2H); 4.48(d, 1H); 4.65(d, 1H); 4.9–5.0(m, 1H); 6.97–7.18(m, 4H); 7.38–7.7(m, 7H); 7.85(d, 2H) |
| 35 | chiral | 207–209 | (in DMSO-d6): 3.05–3.15(m, 2H); 4.45–4.7(d, d, 2H); 4.9(m, 1H); 7.1–8.0(m, 12H); 12.8(s, 1H); |
| 36 | chiral |  | 3.1(m, 2H); 4.6(m, 2H); 4.90(d, 1H); 7.0–8.0(2m, 12H) |
| 37 | chiral |  | 3.0–3.2(m, 2H); 4.55(dd, 2H); 4.90 (d, 1H); 7.05–7.25(m, 4H); 7.1–8.0 (3m, 12H) |

TABLE 2-continued

Carboxylic acids of the formula I

| Ex. | Structure | mp. (° C.) | ¹H NMR |
|---|---|---|---|
| 38 | chiral | | 3.0–3.2(m, 2H); 4.55(dd, 2H); 4.90 (d, 1H); 7.05–7.25(m, 4H); 7.1–8.0 (3m, 12H) |
| 39 | chiral, ClH | 122–135 amorphous | (in MeOH-d4): 3.02–3.36(m, 2H d, s, 6H); 4.57(d, 1H); 4.72(d, 1H); 4.85–5.01(m, 1H); 7.03–7.19(m, 4H); 7.54 (d, 2H); 7.7–7.98(m, 6H) |
| 40 | 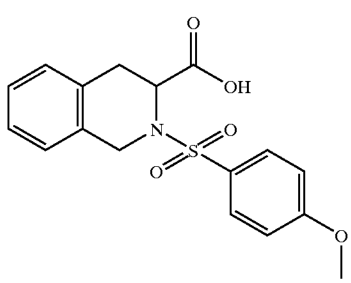 | | 2.9–3.2(m, 2H); 3.8(s, 3H); 4.3–4.6 (dd, 2H); 4.8(m, 1H); 7.1(m, 6H); 7.8(d, 2H) |
| 41 13b | chiral | 147 | (in DMSO-d6): 3.0–3.15(m, 2H); 4.4–4.65(d, d, 2H); 4.8–4.9(m, 1H); 7.0–7.9(m, 13H); 12.9(s, 1H); |
| 42 | chiral | 167–168 | (in DMSO-d6): 3.0–3.15(m 2H); 4.4–4.65(m, 2H); 4.85(m, 1H); 7.0–7.9(m, 12H); 12.9(s, 1H); |

TABLE 2-continued

Carboxylic acids of the formula I

| Ex. | Structure | | mp. (° C.) | ¹H NMR |
|---|---|---|---|---|
| 43 | [structure] | chiral; with triethanolamine (N(CH₂CH₂OH)₃) | oil | (in DMSO-d6): 2.4–2.7(m, 6H)2.8–3.0(m, 2H); 3.3–3.5(m, 6H); 4.4–4.6(m, 2H); 4.7(m, 1H); 7.0–7.9(m, 13H) |
| 44 | [structure] | chiral | | (in DMSO-d6): 2.9–3.2(m, 2H); 4.4–4.65(d, d, 2H); 4.85(m, 1H); 5.15(s, 2H); 7.0–7.9(m, 12H); 12.9(s, 1H); |
| 45 | [structure] | chiral | oil | (in DMSO-d6): 3.0–3.2(m, 2H); 4.4–4.75(d, d, 2H); 4.9(m, 1H); 7.1–8.1(m, 13H); 12.9(s, 1H) |
| 46 | [structure] | chiral | 218–219 | (in DMSO-d6): 3.0–3.1(m, 2H); 4.45–4.8(d, d, 2H); 4.9–5.0(m, 1H); 7.0–8.8(m, 1H); 12.8(s, 1H); |
| 47 | [structure] | | 211–213 amorphous | 3.0–3.2(m, 2H); 4.5(d, 1H); 4.72(d, 1H); 4.9–5.05(m, 1H); 7.05–7.25(m, 4H); 7.6–7.75(m, 3H); 7.85–8.05(m, 2H); 8.2–8.4(m, 3H); 12.9(sb, 1H) |

TABLE 2-continued

Carboxylic acids of the formula I

| Ex. | Structure | mp. (° C.) | ¹H NMR |
|---|---|---|---|
| 48 | 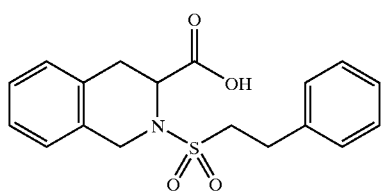 | | 3.0; 3.2(2m, 4H); 3.3–3.6(m, 2H); 4.5–4.75(dd, 2H); 4.8("t", 1H); 7.1–7.4(m, 9H) |
| 49 | 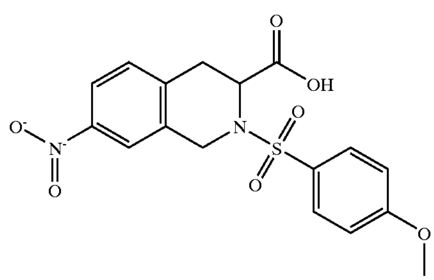 | | 3.0–3.3(m, 2H); 3.8(s, 3H); 4.45–4.85(dd, 2H); 4.85(m, 1H); 7.0; 7.4; 7.8(3d, 6H); 8.0(dd, 1H); 8.1(d, 1H) |
| 50 | 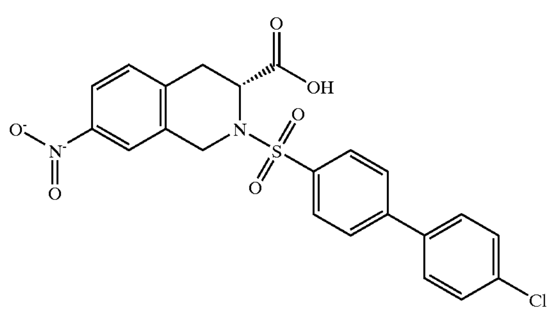 | chiral | 3.3(m, 2H); 4.5–4.85(dd, 2H); 5.05 (m, 1H); 7.2–8.1(mm, 11H) |
| 51 | 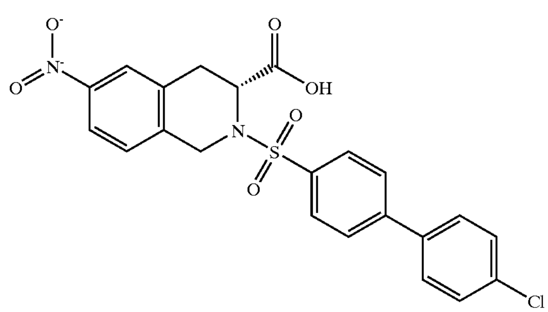 | chiral | 3.3(m, 2H); 4.5–4.8(dd, 2H); 5.05 (dd, 1H); 7.2–8.0(4m, 11H) |
| 52 | 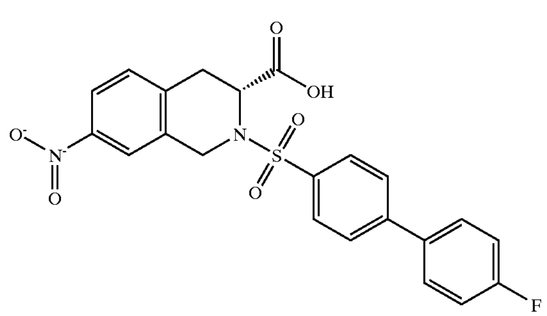 | chiral | 3.1–3.4(m, 2H); 4.5–5.0(dd, 2H); 4.95(m, 1H); 7.2–8.1(2m, 11H) |

TABLE 2-continued

Carboxylic acids of the formula I

| Ex. | Structure | mp. (° C.) | ¹H NMR |
|---|---|---|---|
| 53 | 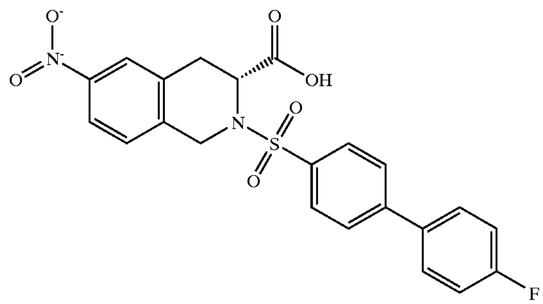 | chiral | 3.1–3.4(m, 2H); 4.5–4.9(dd, 2H); 4.95(m, 1H); 7.2–8.15(2m, 11H) |
| 54 | 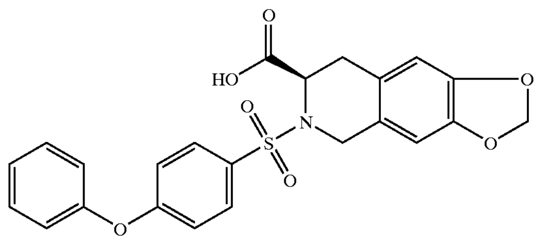 | 226–228 | (in DMSO-d6): 2.8–3.1(m, 2H); 4.3–4.5(d, d, 2H); 4.75(m, 1H); 5.95(s, 2H); 6.7–7.9(m, 11H); 12.9(s, 1H); |
| 55 | 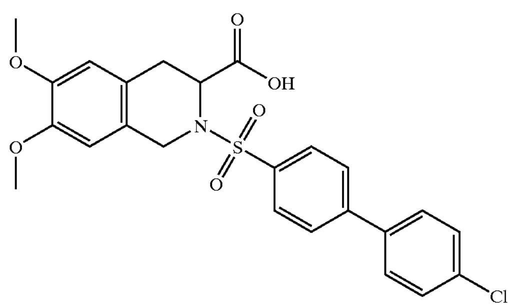 | | 2.9–3.1(m, 2H); 3.8(s, 6H); 4.35–4.8(dd, 2H); 4.90(d, 1H); 6.7; 6.8 (2s, 2H); 7.55; 7.80(2d, 4H); 7.9(m, 4H) |
| 56 | 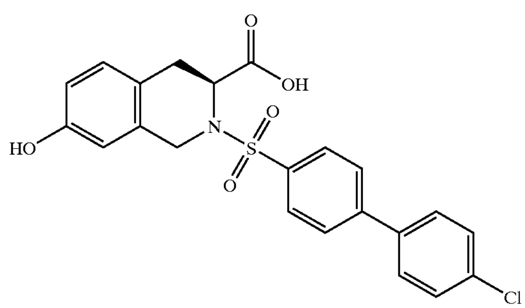 | | 2.8–3.1(m, 2H); 4.3–4.6(dd, 2H); 4.85(m, 1H); 6.5(m, 2H); 6.95(d, 1H); 7.5–8.0(m, 8H); 8.5; 8.8(2s, 1H) |
| 57 | 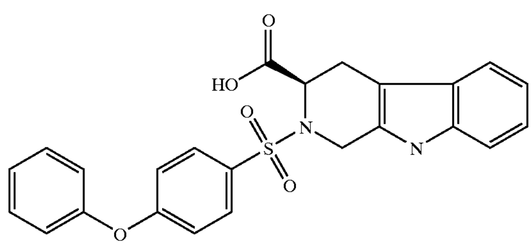 | chiral 115 | (in DMSO-d6): 3.3–3.45(m, 2H); 4.4–4.85(m, 2H); 5.8–5.9(m, 1H); 6.85–7.9(m, 13H); 10.7(s, 1H); |

TABLE 2-continued

Carboxylic acids of the formula I

| Ex. | Structure | mp. (° C.) | $^1$H NMR |
|---|---|---|---|
| 58 | 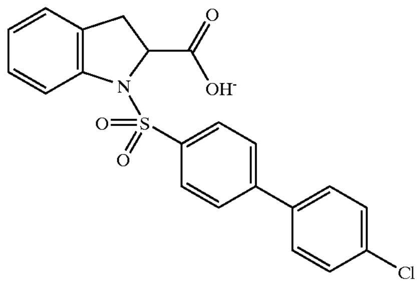 | | 3.1; 3.4(2m, 2H); 5.05(m, 1H); 7.0–8.0(m, 12H) |
| 59 | 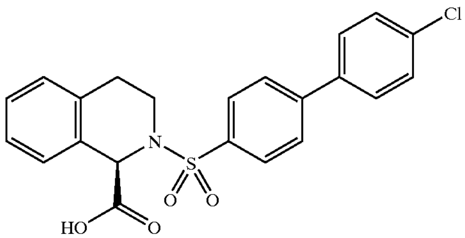 | | 2.8–3.0(m, 2H); 3.5–3.8(m, 2H); 4.3 (s, 1H); 7.1–8.0(mm, 12H) |
| 60 | 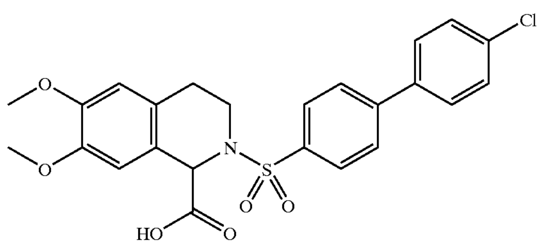 | | 2.7–2.9(m, 2H); 3.4–3.8(m, 2H); 3.8 (2s, 6H); 5.4(s, 1H); 6.7; 6.9(2s, 2H); 7.55; 7.80(2d, 4H); 7.9(s, 4H) |

Pharmacological Examples

Preparation and determination of the enzymatic activity of the catalytic domains of human stomelysine and of neutrophil collagenase.

The two enzymes were prepared according to Ye et al., (Biochemistry 31 (1992) 11231-5). To measure the enzyme activity or enzyme inhibitor action, 70 µl of buffer solution and 10 µl of enzyme solution are incubated for 15 minutes with 10 µl of a 10% strength (v/v) aqueous dimethyl sulfoxide solution, which optionally contains the enzyme inhibitor. After addition of 10 µl of a 10% strength (v/v) aqueous dimethyl sulfoxide solution which contains 1 mmol/l of the substrate, the enzyme reaction is monitored by fluorescence spectroscopy (328 nm (ex)/393 nm(em)). The enzyme activity is shown as extinction increase/minute. The IC50 values listed in Table 3 were determined as the inhibitor concentration which leads to a 50% inhibition of the enzyme. The buffer solution contains 0.05% of Brij (Sigma, Deisenhofen, Germany) and also 0.1 mol/l of tris/HCl, 0.1 mol/l of NaCl, 0.01 mol/l of CaCl$_2$ (pH=7.5) for the determination of the hydroxamic acids up to and including Example 33, or, for the determination of the carboxylic acids from Example 34, 0.1 mol/l of piperazine-N,N'-bis[2-ethanesulfonic acid] pH=6.5.

The enzyme solution contains 5 µg/ml of one of the enzyme domains prepared according to Ye et al. The substrate solution contains 1 mmol/l of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-NH$_2$ (Bachem, Heidelberg, Germany).

TABLE 3

| Example No. | Stromelysine IC 50 [M] | Neutrophil collagenase IC 50 [M] |
|---|---|---|
| 1 | $3*10^{-7}$ | $2*10^{-8}$ |
| 2 | $2*10^{-8}$ | $2*10^{-10}$ |
| 3 | $3*10^{-8}$ | $2*10^{-9}$ |
| 4 | $7*10^{-7}$ | $1*10^{-7}$ |
| 5 | $6*10^{-6}$ | $3*10^{-7}$ |
| 6 | $5*10^{-7}$ | $3*10^{-8}$ |
| 8 | $3*10^{-6}$ | $2*10^{-7}$ |
| 9 | $4*10^{-7}$ | $8*10^{-7}$ |
| 10 | $3*10^{-7}$ | $1*10^{-7}$ |
| 11 | $4*10^{-7}$ | $7*10^{-8}$ |
| 12 | $4*10^{-7}$ | $2*10^{-7}$ |
| 13c | $2*10^{-8}$ | $2*10^{-9}$ |
| 14 | $3*10^{-8}$ | $2*10^{-9}$ |
| 15 | $1*10^{-7}$ | $1*10^{-8}$ |
| 17 | $1*10^{-7}$ | $2*10^{-8}$ |
| 18 | $3*10^{-8}$ | $3*10^{-9}$ |
| 19 | $2*10^{-6}$ | $3*10^{-7}$ |
| 20 | $1*10^{-8}$ | $1*10^{-9}$ |
| 21 | $2*10^{-8}$ | $2*10^{-9}$ |
| 22 | $3*10^{-8}$ | $8*10^{-9}$ |
| 23 | $8*10^{-8}$ | $8*10^{-9}$ |
| 24 | $6*10^{-8}$ | $2*10^{-8}$ |
| 25 | $4*10^{-7}$ | $3*10^{-7}$ |
| 26 | $6*10^{-6}$ | $3*10^{-7}$ |
| 27 | $3*10^{-8}$ | $4*10^{-9}$ |

TABLE 3-continued

| Example No. | Stromelysine IC 50 [M] | Neutrophil collagenase IC 50 [M] |
|---|---|---|
| 28 | $2*10^{-6}$ | $7*10^{-7}$ |
| 29 | $2*10^{-8}$ | $4*10^{-9}$ |
| 31 | $2*10^{-8}$ | $3*10^{-9}$ |
| 32 | $6*10^{-8}$ | $7*10^{-9}$ |
| 33 | $3*10^{-7}$ | $7*10^{-8}$ |
| 34 | $5*10^{-7}$ | $1*10^{-8}$ |
| 35 | $1*10^{-7}$ | $5*10^{-9}$ |
| 36 |  | $3*10^{-6}$ |
| 39 | $1*10^{-7}$ | $1*10^{-9}$ |
| 41 (13b) | $2*10^{-7}$ | $9*10^{-9}$ |
| 42 | $5*10^{-7}$ | $2*10^{-8}$ |
| 43 | $2*10^{-5}$ | $2*10^{-7}$ |
| 44 | $2*10^{-7}$ | $3*10^{-8}$ |
| 45 | $3*10^{-6}$ | $3*10^{-7}$ |
| 46 | $3*10^{-6}$ | $3*10^{-7}$ |
| 50 | $6*10^{-7}$ | $3*10^{-8}$ |
| 51 | $5*10^{-7}$ | $2*10^{-8}$ |
| 52 | $1*10^{-6}$ | $4*10^{-8}$ |
| 53 | $5*10^{-7}$ | $2*10^{-8}$ |
| 57 | $2*10^{-6}$ | $1*10^{-7}$ |

2. Proteoglycan Degradation Assay

Principle of the Assay:

In the proteoglycan degradation assay, the extent of the degradation of native bovine aggrecan, the most important proteoglycan of the cartilage, is measured. The released proteoglycan fragments are determined using the monoclonal antibody 5-D-4 which recognizes the keratan sulfate side-chains which are located at the carboxy terminal of the G2 domain of aggrecan. Thus, the assay detects primarily pathologically important degradations which take place in the interglobular domain of aggrecan.

After addition of compounds of the formula I and the enzyme in the form of the catalytic domain of stromelysine-1, the amount of hyaluronic acid-bound aggrecan which remains after degradation is measured. The more aggrecan is detected, the lower the residual activity of the enzyme. The concentrations of compounds of the formula I at which the initial enzyme activity (=100% residual activity) is reduced by half (=50% residual activity) is indicated by the IC50 values in Table 3.

Description of the Test Protocol:

Wells of 96 well microtiter plates (Nunc, Maxisorp) each containing 100 μl of hyaluronic acid solution (25 μg/ml of hyaluronic acid (Sigma) in PBS) are incubated at room temperature (RT) for 12 h. The hyaluronic acid solution is removed by suction and the remaining free protein binding sites of the wells are saturated with in each case 100 ml of a 5% strength solution of bovine serum albumin (BSA), 0.05% of Tween20 in PBS at RT for 1 h. The wells are subsequently covered with proteoglycane by incubating the wells with 100 μl each of a solution of bovine nasal proteoglycane (ICI) (200 μg/ml in 1×PBS, 5 mg/ml of BSA, 0.05% of Tween20) at RT for 1 h. The wells are washed twice with 1×PBS, 0.1% Tween20 to remove the free proteoglycanes. Subsequently, for the actual assay, 60 ng of purified catalytic domain of Stromelysine-1 (for the recombinant expression and purification, see Ye et al. (1992)) plus corresponding concentrations of the inhibitor to be tested in 100 μl of degradation buffer (100 mM MES pH 6.0, 100 mM NaCl, 10 mM CaCl$_2$, 0.05% of Brij) are pipetted into the wells and incubated at RT for 3 h. The wells are washed twice with 1×PBS, 0.1% of Tween20 and then incubated with 100 μl of a solution of the detection antibody (monoclonal antibody done 5-D-4 (ICI), immunoreactive with the keratan sulfate side-chains of the proteoglycane, dilution 1:1000 in 1×PBS, 5 mg/ml BSA, 0.05% Tween20). The wells are washed twice with 1×PBS, 0.1% of Tween20, after which the immune reaction of the bound detection antibodies is carried out using 100 μl per well of an antibody solution for detection (goat anti Maus IgG, labeled with peroxidase (Dianova), diluted 1:1000 in 1×PBS, 5 mg/ml of BSA, 0.05% of Tween20) at RT for 1 h. The wells are again washed twice (as above), and the color reaction is then initiated using 100 μl each of 2 mg/ml of ABTS, activated with H$_2$O$_2$. The reaction products are measured in an ELISA reader at a wavelength of 405 mm. The results are shown in Table 4.

TABLE 4

| Example No. | Proteoglycane degradation IC50 [M] |
|---|---|
| 2 | $8.5*10^{-8}$ |
| 9 | $1.6*10^{-6}$ |
| 13c | $5.1*10^{-8}$ |
| 14 | $6.7*10^{-9}$ |
| 18 | $4.1*10^{-8}$ |
| 20 | $1.3*10^{-7}$ |
| 21 | $6.5*10^{-8}$ |
| 29 | $2.5*10^{-8}$ |

What is claimed is:

1. A compound of formula I

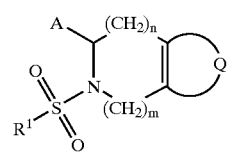

(I)

or an optionally stereoisomeric form of the compound of the formula I, or a physiologically tolerable salt of the foregoing, where in the case (i):

R$^1$ is a radical of formula IV

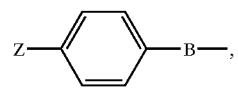

(IV)

where Z is a radical of a heterocycle or a substituted heterocycle; and

Q as part of the compound of formula I is (1) structural moiety VI

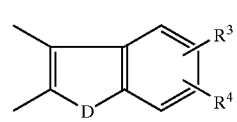

(VI)

where D is NR$^4$ or S;

(2) structural moiety VII

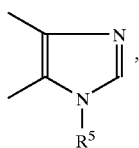
(VII)

(3) structural moiety VIII

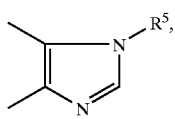
(VIII)

(4) structural moiety IX,

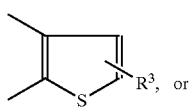
(IX)

(5) structural moiety X

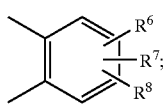
(X)

$R^3$ and $R^4$ are identical or different and each is
(1) a hydrogen atom,
(2) $(C_1-C_5)$-alkyl,
(3) $(C_1-C_5)$-alkoxy,
(4) halogen,
(5) hydroxyl, or
(6) —O—C(O)—$R^{10}$, where $R^{10}$ is
$(C_1-C_6)$-alkyl,
$(C_3-C_6)$-cycloalkyl,
benzyl, or
phenyl,
$R^5$ is
(1) a hydrogen atom,
(2) $(C_1-C_5)$-alkyl, or
(3) benzyl; and
$R^6$, $R^7$, and $R^8$ are identical or different, and each is
(1) a hydrogen atom, or
(2) 2.1 hydroxyl,
2.2 —O—$R^{10}$, where $R^{10}$ is
2.2.1 $(C_1-C_6)$-alkyl,
2.2.2 $(C_3-C_6)$-cycloalkyl,
2.2.3 benzyl, or
2.2.4 phenyl,
2.3 —COOH,
2.4 $(C_1-C_6)$-alkyl,
2.5 $(C_3-C_6)$-cycloalkyl-O—$(C_1-C_4)$-alkyl,
2.6 halogen,
2.7 —CN,
2.8 —$NO_2$,
2.9 —$CF_3$,
2.10 —O—C(O)—$R^{10}$, where $R^{10}$ is as defined above,
2.11 —O—C(O)-phenyl, mono- or disubstituted by $R^3$,
2.12 —C(O)—O—$R^{10}$, where $R^{10}$ is as defined above,
2.13 methylenedioxo,
2.14 —C(O)—$NR^{11}R^{12}$, where
$R^{11}$ and $R^{12}$ are identical or different and each is
2.14.1 a hydrogen atom,
2.14.2 $(C_1-C_4)$-alkyl,
2.14.3 benzyl or
2.14.4 $R^{11}$ and $R^{12}$ together with the linking nitrogen atom form a pyrrolidine, piperidine, morpholine or piperazine radical, or
2.15 —$NR^{13}R^{14}$, where $R^{13}$ is a hydrogen atom or $(C_1-C_4)$-alkyl, and $R^{14}$ is
2.15.1 a hydrogen atom,
2.15.2 $(C_1-C_4)$-alkyl,
2.15.3 benzyl,
2.15.4 —C(O)—$R^{10}$, or
2.15.5 —C(O)—O—$R^{10}$, and $R^{10}$ is as defined above;

n is zero, 1, or 2, and m is zero, 1, or 2, such that the sum of n and m is 1, 2, or 3; and X is
(1) a covalent bond,
(2) —O—,
(3) —S—,
(4) —S(O)—,
(5) —$S(O)_2$—,
(6) —C(O)—, or
(7) —C(OH)—;

Y is
(1) —O— or
(2) —S—;

A is HO—NH—C(O)— or HO—C(O)—; and

B is
(1) —$(CH_2)_q$—, where q is zero, 1, 2, 3 or 4, or
(2) —CH=CH—.

2. A compound of formula I as claimed in claim 1, wherein

Z is a radical of a heterocycle or a substituted heterocycle chosen from
3.1 pyrrole,
3.2 thiazole,
3.3 pyrazole,
3.4 pyridine,
3.5 imidazole,
3.6 pyrrolidine,
3.7 piperidine,
3.8 thiophene,
3.9 oxazole,
3.10 isoxazole,
3.11 morpholine and
3.12 piperazine.

3. A compound of formula I as claimed in claim 1, where q in the definition of B is zero;
X is an oxygen atom or a covalent bond; and
$R^6$, $R^7$ and $R^8$ are identical or different and each is
(1) a hydrogen atom,
(2) methoxy,
(3) methylenedioxo,
(4) amino, or
(5) hydroxyl.

4. A compound of formula I as claimed in claim 1, wherein the central carbon atom between amino and hydroxamic acid group is present as R enantiomer.

5. A compound of formula I as claimed in claim 2, wherein the central carbon atom between amino and hydroxamic acid group is present as R enantiomer.

6. A compound of formula I as claimed in claim 3, wherein the central carbon atom between amino and hydroxamic acid group is present as R enantiomer.

7. A compound of formula I as claimed in claim 1 wherein n is 1 and m is 1.

8. A compound of formula I as claimed in claim 1 wherein m and n are zero, 1, or 2 and where the meanings of n and m are not identical.

9. A pharmaceutical composition comprising an efficacious amount of a compound as claimed in claim 1 and at least one physiologically acceptable auxiliary or excipient.

10. A pharmaceutical composition comprising an efficacious amount of a compound as claimed in claim 2 and at least one physiologically acceptable auxiliary or excipient.

11. A pharmaceutical composition comprising an efficacious amount of a compound as claimed in claim 3 and at least one physiologically acceptable auxiliary or excipient.

12. A pharmaceutical composition comprising an efficacious amount of a compound as claimed in claim 4 and at least one physiologically acceptable auxiliary or excipient.

13. A pharmaceutical composition comprising an efficacious amount of a compound as claimed in claim 5 and at least one physiologically acceptable auxiliary or excipient.

14. A method for treating a patient experiencing one or more disorders in the course of which an increased activity of matrix-degrading metalloproteinases is involved, the method comprising administering to the patient an efficacious amount of a compound of formula I, or an optionally stereoisomeric form thereof, or a physiologically tolerable salt of the foregoing, as claimed in claim 1.

15. A method for treating a patient experiencing one or more disorders, the method comprising administering to the patient an efficacious amount of a compound of formula I, or an optionally stereoisomeric form thereof, or a physiologically tolerable salt of the foregoing, as claimed in claim 1, wherein said one or more disorders are chosen from:

(1) disorders of connective tissue; and (2) chronic disorders of locomotory apparatus; and (3) disorders of the bone metabolism and degenerative joint disorders; and (4) disorders comprising one or more of ulceration, artherosclerosis, and stenoses; and (5) disorders involving inhibition of the release of tumor necrosis factor; and (6) inflammations, carcinomataceous disorders, formation of tumor metastases, cachexia, anorexia, and septic shock.

16. A method as claimed in claim 15, wherein the disorders of connective tissue are chosen from collagenoses, periodontal disorders, and wound healing disorders.

17. A method as claimed in claim 15, wherein the chronic disorders of locomotory apparatus are chosen from inflammatorily, immunologically, and metabolically related acute and chronic arthritis, arthropathies, and myalgias.

18. A method as claimed in claim 15, wherein the disorders of the bone metabolism and degenerative joint disorders are chosen from osteoarthrosis, spondylosis, chondrolysis after joint trauma, and relatively long joint immobilization after one or more of meniscus injuries, patella injuries, and ligament tears.

19. A process for the production of a pharmaceutical composition as claimed in claim 9, which comprises bringing into a suitable administration form a compound of formula I and at least one physiologically acceptable auxiliary or excipient.

* * * * *